United States Patent [19]
Winkler

[11] Patent Number: 6,098,625
[45] Date of Patent: Aug. 8, 2000

[54] PROPHYLACTIC HAVING INTEGRAL EXTENSIONS AND A FLUID ABSORBING MEANS

[75] Inventor: John A. Winkler, Tucson, Ariz.

[73] Assignee: John Winkler, Tucson, Ariz.

[21] Appl. No.: 09/232,476

[22] Filed: Jan. 15, 1999

[51] Int. Cl.[7] ........................................... A61F 6/02
[52] U.S. Cl. .......................... 128/842; 128/844; 128/918
[58] Field of Search .................................. 128/842, 844, 128/918; 604/347–353

[56] References Cited

U.S. PATENT DOCUMENTS

| 3,648,700 | 3/1972 | Warner | 128/842 |
| 4,320,752 | 3/1982 | Comparetto | 128/132 R |
| 4,821,742 | 4/1989 | Phelps | 128/844 |
| 4,865,595 | 9/1989 | Heyden | 604/352 |

*Primary Examiner*—Michael A. Brown

[57] ABSTRACT

A prophylactic which sits atop the glans penis, ahering to the annular region about the urethral opening and having integrally attached, adhesive covered extensions which lie adhered along the surface of the glans penis. The invention is manipulated during installation by holding a semi-rigid support structure which is either removable from the backside of the adhesive covered annular surface and extensions or integral to the same annular surface and extensions. An absorbent material is provided in the reservoir of the device for absorbing the ejaculate from the user.

20 Claims, 4 Drawing Sheets

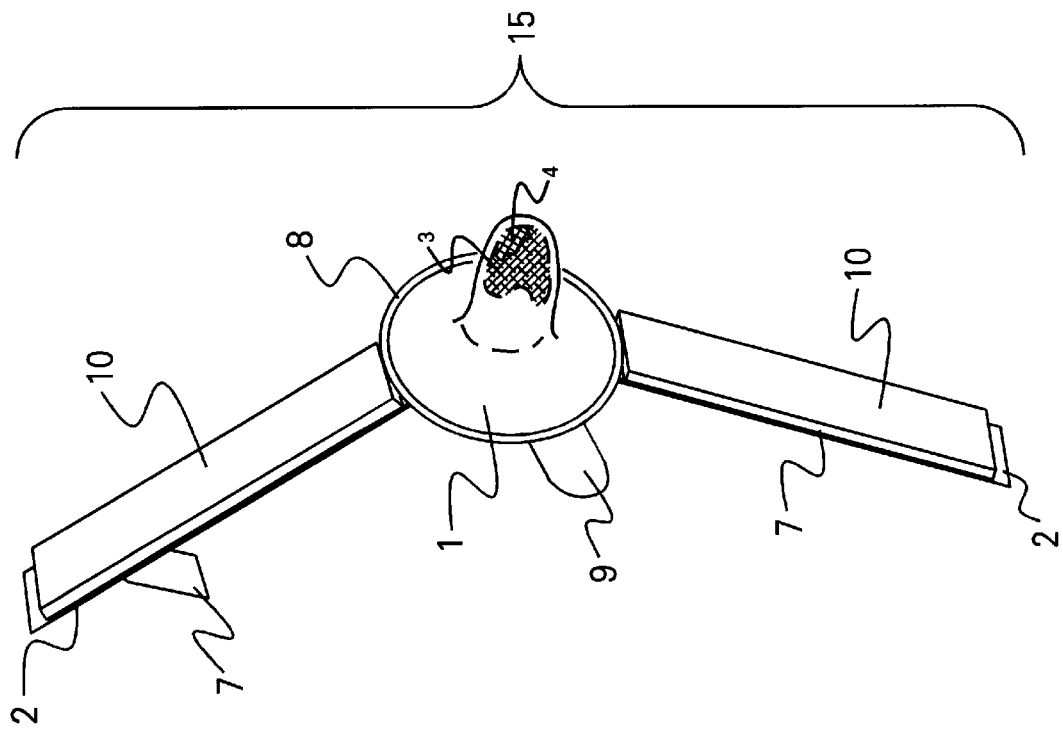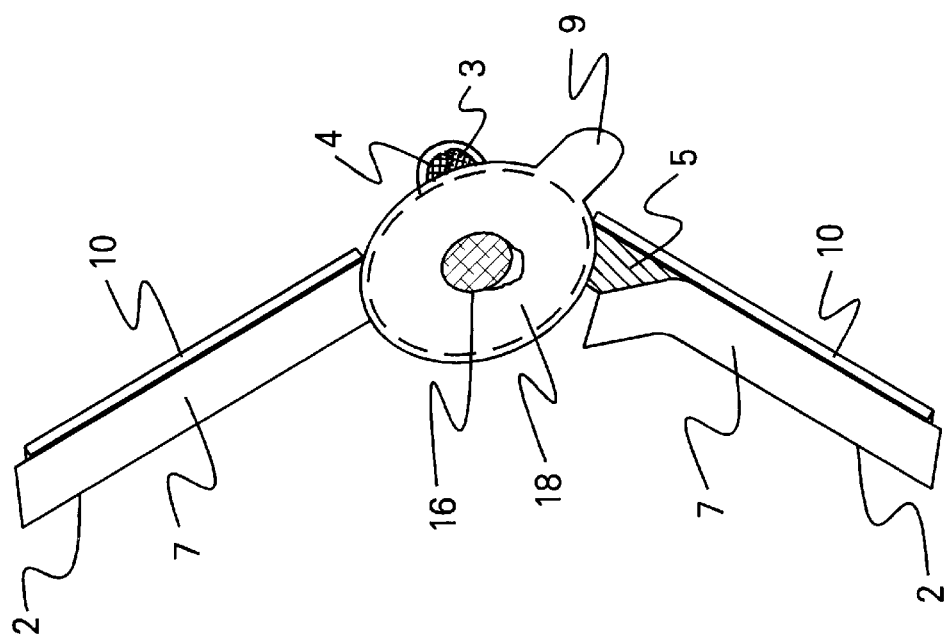
FIG. 1b
FIG. 1a

PROPHYLACTIC HAVING INTEGRAL EXTENSIONS AND A FLUID ABSORBING MEANS

FIELD OF THE INVENTION

This invention relates to contraceptive and prophylactic devices for preventing pregnancies and the transmission of sexually transmitted diseases during sexual intercourse, and more particularly to condoms, micro-condoms and penile caps.

BACKGROUND OF THE INVENTION

Numerous prophylactics have been presented for patent which cover the length of the tumescent male organ or adhere to the glans of the penis about the urethral opening to seal the urethral opening against foreign bodily fluids and microorganisms. Those prophylactics which cover the length of the tumescent penis interfere with frictional stimulation. Additionally, the device may slip off completely when the penis assumes a flaccid condition after ejaculation. This slippage may result in seminal fluid leaking out of the prophylactic. Another objection to the use of conventional condoms is that their thinness tends to allow them to tear or leak during use, thereby permitting the exchange of bodily fluid between partners. The leakage problem can be diminished by manufacturing the condom of thicker material, but such a method will further lower the level of stimulation afforded the user.

Those prophylactics, known as penile caps or microcondoms, which adhere near the tip of the glans penis, such as U.S. Pat. Nos. 5,421,350, 4,869,269, 4,821,742, 3,677,225 and 5,458,114 significantly reduce the penile glans and shaft surface area deprived of frictional stimulation. Penile caps which adhere only to the glans area immediately surrounding the urethral orifice risk being pulled off completely or partially, either way compromising the biological barrier formed by the adhesive seal encircling the urethral opening. While minimizing bonding surface area is preferrable to maximize frictional stimulation, maximizing bonding surface area is preferrable from a failure prevention perspective.

U.S. Pat. Nos. 4,869,269, 4,821,742, 3,677,225 and 5,458,114 all disclose a microcondom or penile cap which is formed closely to the shape of the glans and seals directly to the area immediately surrounding the urethral opening, thereby reducing the chance for fluid exchange. However, all four of these devices could suffer localized failure of the adhesive seal or be pulled off of the glans during coitus by cyclic tensile forces because of the minimized bonding area.

U.S. Pat. No. 4,869,269 provides a seminal reservoir that is much too large, rigid and projecting for the comfort of the user's partner. Additionally, the design of this structure has poor stiffness against radially applied compressive forces, such as those developed by squeezing together the thumb and forefinger during typical application of the device, presenting the likelihood of collapsing its structure during application and enabling two points diametrically opposed on the adhesive coated surface to contact each other, bond, and render the condom unuseable.

In a similar design, U.S. Pat. No. 5,458,114 offers an adhesive condom which also minimizes the area of the glans deprived of sensation but once again it is designed as a structure which could easily collapse during handling, thus enabling two points diametrically opposed on the adhesive coated surface to contact each other and render the condom unuseable. Additionally, the proposed bladder and bowl pieces of the design are suggested to be bonded together unless they are able to be manufactured as a single unit. Having multiple parts joined together by assembly procedures reduces the reliability of the device and presents the possibility of failure if a bond joint is poorly formed during manufacture or comes apart during use because the geometrically unstable bladder has become wedged between nearby surfaces within the receptive body cavity or instead between the penis and the body cavity after bladder deployment. Furthermore, this design exposes the deployed bladder to a pattern of cuts in the outer envelope which can develop localized areas of high stress in the thin bladder material again presenting the opportunity to tear the bladder material if it were to become wedged and pulled. Such a tear would completely defeat the purpose of the contraceptive prophylactic.

U.S. Pat. Nos. 4,821,742 and 3,677,225 are similar in design and are designed to adhere only to the area immediately surrounding the urethral orifice, or meatus, and are prone to failure due to the very small surface area adhered to the glans of the penis which must oppose cyclic tensile and shear forces encountered during coitus. Additionally, no mounting tool is described as being used with the invention of U.S. Pat. No. 4,821,742 and the flimsy nature of the base portion of the invention invites the opportunity for the user to collapse and bond the adhesive surfaces of the base portion together rendering the device unapplicable or unintentionally leave a crease in the base material during application which subsequently becomes a leakage path for ejaculate. While U.S. Pat. No. 3,677,225 does describe a tool for applying the prophylactic, the tool is in two separate halves which offers the unsteady user the unintentional opportunity to apply the device with leakage paths in the form of creases or wrinkles in the prophylactic material as it is bonded down.

U.S. Pat. No. 5,421,350 discloses a micro-condom or penile cap which covers the glans rather than the greater part of the penis. Although the device is designed toward increased user stimulaton, its coverage of the entire glans limits frictional stimulation around the most sensitive part of the penis. Additionally, the design of this structure has poor stiffness against radially applied compressive forces, such as those developed by squeezing together the thumb and forefinger during typical application of the device, presenting the likelihood of collapsing its structure during application and enabling two points diametrically opposed on the adhesive coated surface to contact each other, bond, and render the condom unuseable.

The proposed invention resembles a penile cap in the fact that it adheres to the tip of the glans of the penis to form a leakproof seal around the urethral orifice. However, unlike other penile caps, the proposed invention has integrally attached, adhesive-coated strips for handling and force distribution which lie adhered along the surface of the glans. These strips serve to oppose tensile forces acting on the perimeter of the adhered area and in doing so prevent the possible failure of the adhesive seal which is a probable scenario in other designs because of cyclical tensile loading. The strips only cover small landings on the glans surface leaving the rest of the glans surface area, especially the highly sensitive coronal ridge, exposed to unimpeded frictional stimulation offering improvement over rolldown, full length prophylactics. The force distribution strips disperse the tensile load acting on the penile cap without overly depriving the user of frictional stimulation to the major surface area of the glans. In addition to the force distribution strips, the proposed invention also has a fluid absorbing means in the bladder portion of the invention to absorb and contain male urethral discharge which significantly increases the probability of maintaining a functional adhesive seal. The bonding of the prophylactic to the user is achieved in a two part process. In the first phase the user applies a liquid adhesive to the skin of the glans and penile shaft in areas which the prophylactic will be bonded. In the second phase adhesive preapplied to selected surfaces on the prophylactic is exposed and mated to the cured adhesive coating on the skin, forming the bondline between the glans skin and the prophylactic. After usage the bondline is broken by applying a hypo-allergenic solvent means of removal known in the art which dissolves the liquid adhesive means of attachment dried on the skin. The proposed invention is also contoured to the shape of the tumescent glans during application by using a membrane tensioning means which holds the substantially annular surface of the device in a taut condition so that it can be stretched out over the contour of the glans penis during bonding.

SUMMARY OF THE INVENTION

The primary objective of the invention is to serve as a seal over the urethral opening of the male sex organ, with the capability to withstand tensile and shearing forces significantly larger than those which could be expected under normal coital activity, to effectively prevent the exchange of bodily fluids between partners. A second objective of the invention is to provide a contraceptive penile cap prophylactic which is easy to handle, install and remove. A third objective of the invention is to place near the urethral orifice a very flexible, collapsible bladder with absorbent means which does not discomfort the user or partner during coitus but is capable of expanding as necessary to contain ejaculate.

To achieve the first objective, the proposed invention resembles a penile cap which seals over the urethral opening similar to the prior art with the exception that a plurality of extensions of the prophylactic material extend radially outwardly from and beyond the substantially annular flange of the device to provide more adhesion surface to bond to the surface of the glans and distribute any tensile or shearing loading over a greater surface area. The geometry of the penile cap is that which is suitable to form a seal, such as an annular seal, encircling the urethral opening and serving as an enclosure over the urethral opening, preventing biological microorganisms from entering the urethral opening, and to also connect two or more radial force distribution extensions to the penile cap geometry. The prophylactic itself is made of any pliable material known in the art to be suitable for the application such as synthetic latex. A medical grade adhesive material know in the art, such as Monsanto Gelva Acrylic Water-based Medical Grade Adhesive 2222, or Fitchburg 545 free film coated onto a thermoformable polyester liner, or 3M Medical Transfer Film coats the proximal surface of the radial extensions of the device and the proximal surface of the substantially annular flange of the device. A second medical grade liquid adhesive known in the art, such as Mastisol, coats selected portions of the penile shaft and glans. The adhesive coating on the proximal surface of the prophylactic bonds to the dried adhesive coating on the skin to adhere the prophylactic to the glans so the prophylactic completely encloses the urethral opening and prevents biological microorganisms from entering the urethra. The adhesive coating along the proximal surface of each of the radial extensions adheres the extensions to the glans and shaft of the penis to distribute tensile and shearing forces acting on the prophylactic thereby ensuring continuous, proper adhesion during coitus. The adjustment for the length of diffent male sex organs is made possible by applying the radial extension strips in two parts. After applying the liquid adhesive to the skin small lengths of the extension strips are bonded to the penile shaft near the base of the penis. The substantially annular portion of the device and the extension strips attached to that portion are then bonded to the tumescent male member such that the extension strips of the device overlap the small lengths of extension strips near the base of the penis. The device is removed from the glans after coitus by peeling it off, as an adhesive coated bandage is removed, or by using an approved, non-injurious, hypoallergenic adhesive solvent, such as Detachol or other noninjurious means known in the art, and then the prophylactic is disposed of still containing the captured ejaculate.

To achieve the second objective a support, if removable, is in contact with the distal surface of the prophylactic along the radial extensions and also about the distal surface of the annular region encircling the urethral area of the glans to lend support to these areas while the prophylactic is being handled. The support of the distal surface of the annular region is able to be a hoop such that the annular region remains stretched out during application but can be shaped to conform to the glans contour by simply pressing the tumescent glans against the proximal surface of the stretched annular portion of the prophylactic. Alternatively, if the supporting structure is integrally manufactured as part of the prophylactic, the same annular region and radial extension areas are still supported during handling, but the integral supporting structure is not removed until the prophylactic itself is removed. Having the supporting structure integral to the device does not cause additional duress for either partner as an integral supporting structure could be manufactured to be thin yet semi-rigid supports from techniques known in the art such as latex coating of either wire or plastic semi-rigid hoops. Semi-rigid in this application implies not being easily deformed under the ordinary handling practices of such an installation procedure but deformable by greater manual dexterity forces.

To achieve the third objective a very-thin-walled bladder is integrally formed to the main body annular surface for the purpose of collecting ejaculate. The thin-wall bladder is able to expand as necessary to contain ejaculated semen. The thin-wall construction of the bladder allows it to deform as necessary to prevent discomfort or injury caused by compressive forces generated from contacting body cavity walls. A collapsible absorbent material known in the art, such as cotton fabric or synthetic sponge, is placed inside of the bladder to absorb any seminal fluid discharged from the male urethra during coital activity. The absorbent material helps to contain the discharge which is important for preventing hydrodynamic wedging of urethral discharge into the bondline of the adhesive if the prophylactic were to be compressed between the glans and a wall of the receptive body cavity. Hydrodynamic wedging will encourage premature failure of the bondline.

This device affords the user more frictional stimulation than roll-down condoms or glans-covering penile caps but without the clumsy handling issue or the questionable reliability of those penile caps which adhere only to a small annular region around the urethral opening of the glans.

BRIEF DESCRIPTION OF THE DRAWINGS

FIG. 1a shows a rear isometric view of the prophylactic having integral extensions, a fluid absorbing means and a removable support structure according to the invention.

FIG. 1b shows a front isometric view of the prophylactic having integral extensions, a fluid absorbing means and a removable support structure according to the invention. Material has been cut away from some areas for clarity of illustration. Some items in FIGS. 1a and 1b are exploded away or peeled back from the main body of the invention for purpose of illustration clarity.

DESCRIPTION OF THE PREFERRED EMBODIMENTS OF THE INVENTION

Figure 2:
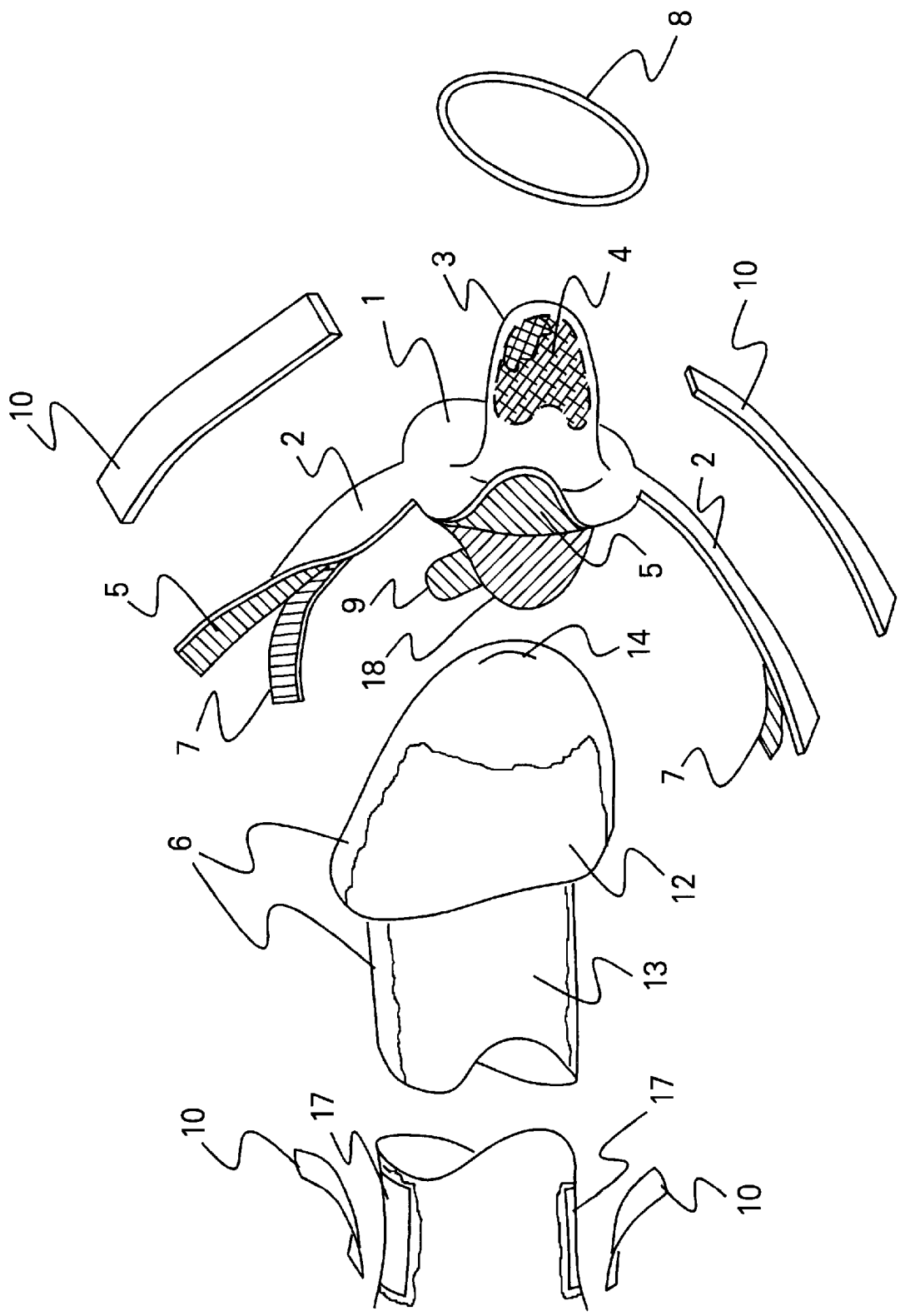
FIG. 2 shows an exploded front isometric view of the prophylactic having integral extensions, a fluid absorbing means and a removable means of support.

Referring to the drawings, FIGS. 1a and 1b show the prophylactic having integral extensions, a fluid absorbing means and a removable support structure as it would be prepared for the user. Similar reference numbers denote similar elements throughout the several views. The overall structure which is the prophylactic is generally designated by the reference number 15. The prophylactic device 15 consists of a reservoir or containment means 3 and several finger-shaped radial extensions 2 attached to a single substantially annular connection flange 1 having an orifice or through-passage 16 leading to the opening of the reservoir 3. The extensions 2 are provided to facilitate handling of the prophylactic and to improve force distribution during use. Along the distal outer surface of each of the radial extensions 2 are removably attached, semi-rigid means of radial support 10 to assist handling. The membrane tensioning hoop means of contouring 8 prevents the flange 1 from collapsing while it is being adhered to the glans 12. The hoop 8 and the semi-rigid radial supports 10 are removably attached to the distal surfaces of the flange 1 and radial extensions 2 using cohesive forces of like materials or using a bonding agent known in the art, such as 3M double stick tape 9416, which remains with the hoop 8 and radial supports 10 when they are removed from the flange 1 and radial extensions 2.

Two different adhesives are used to secure the prophylactic having integral extensions to a user. A pre-applied means of adhesion 5 medical grade adhesive known in the art, such as 3M 1509 Medical Transfer Tape, covers the proximal inner surfaces of the annular flange 1 and the integral extensions 2 and is protected by a first removable protecting means 18 and a second removable protecting means 7. A liquid coating means of adhesion 6 known in the art such as Mastisol or Tincture of Benzoine coats selected topological areas of the glans 12 and penile shaft 13. The bondline between the prophylactic and the glans 12 and shaft 13 is formed by bringing the exposed pre-applied transfer tape 5 into intimate contact with the cured adhesive coating 6 on the glans 12 and shaft 13. The bondline establishes a leakproof seal around the urethral orifice 14.

As shown in FIG. 2, the liquid coating 6 is applied to selected areas of the glans 12 and shaft 13. The first protective means 18 and the second protective means 7 covering the pre-applied transfer film 5 are removed to expose the transfer film 5 for the bonding process.

Figure 3:
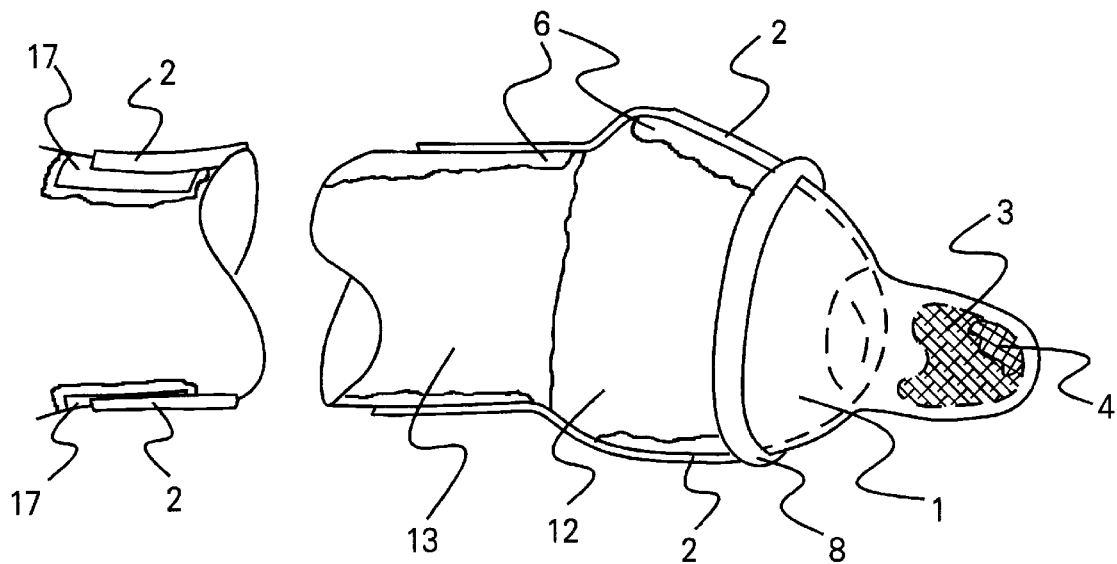
FIG. 3 shows the application process for bonding of the prophylactic having integral extensions, a fluid absorbing means and removable supports to the glans and shaft of a penis.

FIG. 3 shows the bonding process. After exposing the pre-applied film 5 by removing the first protective means 18, the user brings the stretched annular flange 1 still on the membrane tensioning means of contouring 8 into contact with the coated area of the glans 12 immediately surrounding the urethra 14 such that the reservoir orifice 16 centers about the urethral opening 14. By pulling the means of contouring 8 far enough towards the base of the shaft 13, the stretched membrane of the flange 1 will be forced to assume the shape of the glans 12 and will securely adhere to the glans. After the flange 1 is bonded to the glans 12, the membrane tensioning means 8 is removed from the distal surface of the flange 1. The next process is to adhere the integral extensions 2 of the device to the glans 12 and shaft 13. The second removable protective means 7 is removed to expose the pre-applied film 5 along the integral extensions. To account for the variability in length of the male organ an extension strip section for force distribution 17 is attached near the base of the shaft 13 and the semi-rigid means of support 10 is removed from each section 17 bonded near the base. The integral extension 2 attached to the flange 1 overlaps this additional section by an amount to necessarily permit coverage of the shaft 13 from the glans 12 to the base of the shaft 13. After successfully overlapping the sections 17 and the integral extensions of the force distribution strips 2, the removable semi-rigid supports 10 are pressed against the skin to bring the pre-applied film 5 of the integral extensions 2 and the cured liquid adhesive 6 into intimate contact and then the supports 10 are separated from the integral extensions 2. This bonding operation forms a leakproof seal about the male urethral orifice 14 and places near the orifice 14 a collapsible, expandable reservoir or means of containment 3 and a non-rigid means of absorption 4.

Figure 4:
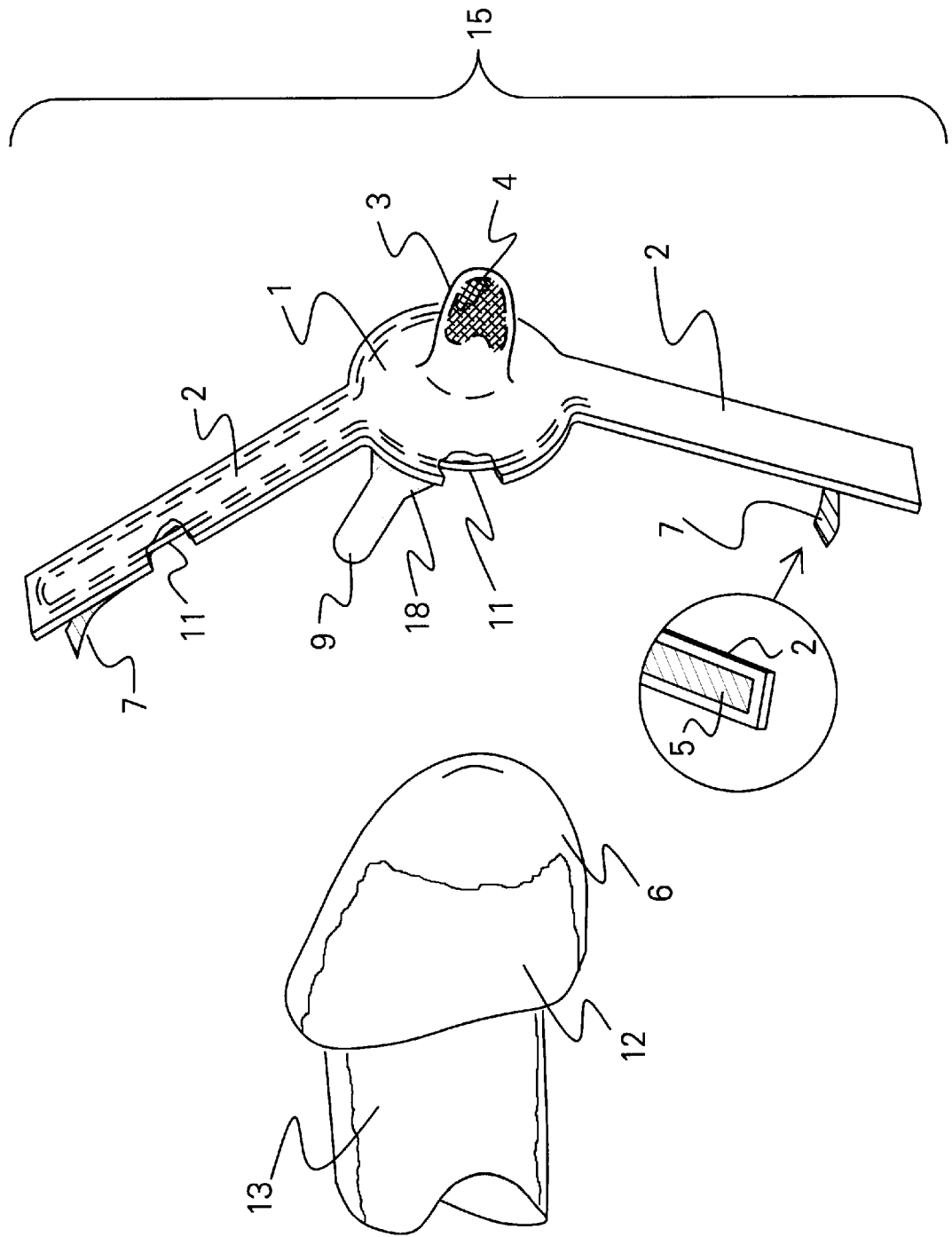
FIG. 4 shows a front isometric view of the prophylactic having integral extensions, a fluid absorbing means, and an integral support structure.

FIG. 4 shows a variation in the design of the device 15 wherein the support structure 11 is not removable but is instead integral to the invention. The integral supports are embedded into the prophylactic material at the time of manufacture and are made out of semi-rigid material such as plastic or thin continuous wire. The integral support structure prevents the annular portion 1 and radial extensions 2 from buckling while being handled during application. The bonding process is similar to the removable support design in that the removable protective means 7 and 18 are removed to expose the pre-applied adhesive 5 and then the proximal surface of the annular portion 1 and the radial extensions 2 are pressed into intimate contact with the cured liquid coating means of adhesion 6 on the glans 12 and shaft 13.

Figure 5:
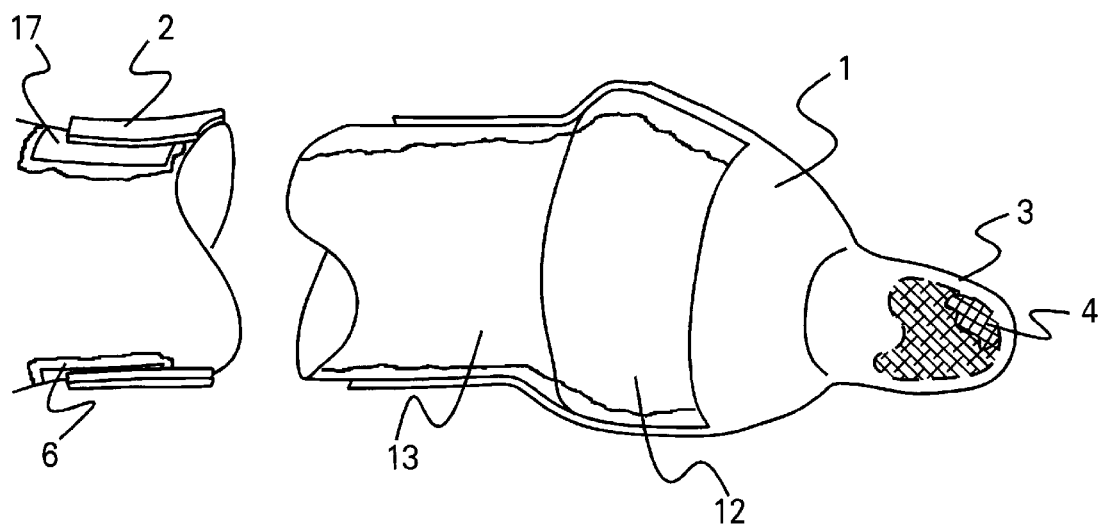
FIG. 5 shows the prophylactic having integral extensions and a fluid absorbing means successfully bonded to the glans and shaft of a penis.

In FIG. 5, a prophylactic 15 has been successfully bonded to the glans 12 and shaft 13 of a penis in a manner which forms a leakproof seal about the male urethral orifice 14 and places near the orifice 14 a collapsible, expandable reservoir means of containment 3 and a non-rigid means of absorption 4.

Referring back to FIG. 1, the preferred embodiment of the device is made of a pliable material such as synthetic latex and has a substantially annular flange 1 which connects a reservoir or containment means 3 to two radial extensions 2 shaped as rectangular strips. The flange 1, being substantially annular, has an outer diameter between 2.0 and 0.5 inches, preferably 1.375 inches; an inner diameter between 1.0 and 0.2 inches, preferably 0.438 inches; and a thickness between 0.1 and 0.0002 inches, preferably 0.004 inches. The reservoir 3 has an orifice diameter 16 between 0.2 and 1.0 inches, preferably 0.438 inches in diameter; a wall thickness between 0.1 and 0.0002 inches, preferably 0.004 inches; and a volume capacity between 0.01 and 1.0 fluid ounces, preferably 0.06 fluid ounces. The radial extensions 2 have a length between 0.25 and 10.0 inches, preferably 4.0 inches; a width between 0.06 and 0.75 inches, preferably 0.188 inches; and a thickness between 0.0002 and 0.1 inches but preferably 0.004 inches. The removable semi-rigid braces 6 have length between 0.25 and 6.0 inches, preferably 4.0 inches; a width between 0.06 and 0.75 inches, preferably 0.188 inches; and a thickness between 0.002 and 0.1 inches, preferably 0.010 inches. The membrane tensioning means of contouring has an inner diameter between 0.5 and 2.0 inches but preferrably 1.375 inches and an outer diameter between 0.55 and 2.5 inches but preferrably 1.625 inches and is between 0.1 and 0.002 inches thick but preferrably 0.010 inches thick. The first removable protective member has a tab 9 integrally attached to it.

Referring back to FIG. 4, the preferred embodiment of the alternative integral semi-rigid supporting frame design has radial extensions 2 with widths of at least 0.06 inches, preferably 0.188 inches, and thicknesses of at least 0.0002 inches, preferably 0.004 inches in those areas not covering framework and preferably 0.020 inches thick in those areas covering framework. All other dimensions for the flange 1 and reservoir 3 are the same as those in the preferred embodiment of the removable support design of FIG. 1.

The first advantage of the prophylactic is the adhesive-coated flange which is small enough in area to cover only the topology of the glans of the penis immediately surrounding the urethral opening thereby reducing the glans area deprived of friction stimulus in comparision to roll-down prophylactics. The adhesive-coated annular flange still has enough area to create an effective sealing surface around the urethral opening for the purpose of forming an enclosure to protect the urethral opening against biological microorganisms.

The second advantage of the prophylactic is that it provides a means to place near the urethral orifice a very flexible, collapsible reservoir and a fluid absorption means which is able to capture and contain ejaculate and which can deform as necessary when subject to compressive forces caused by the device contacting cavity walls, thereby protecting the cavity wall tissue from injury.

The third advantage of the prophylactic is the system of radial extensions which disperse the tensile and shear force loads acting on the prophylactic sealing surface, thereby maintaining the integrity of the seal and greatly improving the reliability of the device over other adhesively attached penile caps bonding only to the area immediately surrounding the urethral opening.

The fourth advantage of the prophylactic is that the flange, the reservoir and the system of radial extensions can be manufactured as a single device of unitary construction, thereby eliminating the introduction of features of assembly, necessary in multiple piece designs, which could compromise the reliability of a prophylactic. Further, integrally-formed semi-rigid spines are also able to be manufactured into the unitary construction design to simplify handling or eliminate handling complications during application.

The fifth advantage of the prophylactic is that because of the ease of application and minimal surface area deprived of frictional stimulation, user apprehension towards the prophylactic device will be appreciably less than that of roll-down prophylactics covering the entire penile shaft, thereby increasing useage of a device which prevents unwanted pregnancies and protects the public against the transmission of venereal diseases.

While the embodiments described herein are at present considered to be preferred, it is understood that various modifications and improvements may be made therein without departing from the invention. The scope of the invention is indicated in the appended claims and all changes that come within the meaning and range of equivalency of the claims intended to be embraced therein.

I claim:

1. A prophylactic device comprising:
   a) containment means with an opening for receiving ejaculate from a user;
   b) a flange attached to said containment means and having a flange through-passage connected to said opening;
   c) a plurality of radial members extending outwardly from and beyond said flange; and
   d) attachment means for securing the prophylactic device to said user's penis.

2. The device of claim 1, wherein said containment means consists of a reservoir integrally formed with said flange as a structure of unitary construction.

3. The device of claim 2, wherein said reservoir is flexible, collapsible and expandable.

4. The device of claim 1, wherein said plurality of radial members and said flange are an integral structure of unitary construction.

5. The device of claim 1, wherein said containment means, said flange, and said plurality of radial members are an integral unit of unitary construction.

6. The device of claim 1, wherein said attachment means includes a first adhesive layer adhesively applied to said flange and to said plurality of radial members.

7. The device of claim 6, wherein said attachment means further includes a second adhesive layer adhesively applied to the user's penis for attachment to said first adhesive layer prior to use of the device.

8. The device of claim 7, wherein said second adhesive layer consists of a fast-curing liquid adhesive.

9. The device of claim 6, further comprising a first removable protective member covering said first adhesive layer over the flange and second removable protective members covering said first adhesive layer over the plurality of radial members.

10. The device of claim 9, further comprising a tab integrally connected to the first removable protective member to facilitate removal thereof from the flange prior to use of the device.

11. The device of claim 1, further comprising a semi-rigid support structure removably affixed to said flange and to each of said radial members.

12. The device of claim 11, wherein said semi-rigid support structure includes a first member having a through passage and being suitable for attachment to an outer surface of the flange and second members suitable for attachment to an outer surface of each of said radial members.

13. The device of claim 1, further comprising an absorption means for absorbing the ejaculate from the user in the containment means.

14. The device of claim 1, wherein said containment means consists of a flexible, collapsible, expandable reservoir integrally formed with said flange; wherein the flange is approximately annular in shape with an outer radius between 0.15 and 1.0 inches, an inner radius of at least 0.125 inches, and a thickness of at least 0.001 inches; wherein said radial members are integrally formed to said flange and each radial member has a length of at least 0.25 inches, a width of at least 0.06 inches, and a thickness of at least 0.001 inches; wherein said attachment means consists of adhesive layers separately applied to an inner surface of said flange and to an inner surface of each of said radial members; and further comprising a semi-rigid support structure that includes a substantially annular member sized approximately to match an outer surface of said annular flange and having a thickness of at least 0.01 inches; and a plurality of elongated members sized approximately to match an outer surface of each of said radial members and having a thickness of at least 0.01 inches.

15. A prophylactic device comprising:
 a) containment means with an opening for receiving ejaculate from a user;
 b) attachment means for securing the prophylactic device to said user's penis; and
 c) absorption means for absorbing the ejaculate from the user in the containment means;
wherein said attachment means includes a first adhesive layer attached to the device, and a second adhesive layer applied to the user's penis for attachment to said first adhesive layer prior to use of the device.

16. The device of claim 15, wherein said attachment means includes a first adhesive layer.

17. The device of claim 16, wherein said attachment means further includes a second adhesive layer applied to the user's penis for attachment to said first adhesive layer prior to use of the device.

18. The device of claim 15, wherein said second adhesive layer consists of a fast curing liquid adhesive.

19. The device of claim 15, further comprising a removable protective member covering said first adhesive layer.

20. The device of claim 19, further comprising a tab integrally connected to the removable protective member to facilitate removal thereof prior to use of the device.

* * * * *